(12) United States Patent
Funk et al.

(10) Patent No.: US 8,410,222 B2
(45) Date of Patent: Apr. 2, 2013

(54) METHOD FOR PRODUCING WATER-ABSORBING POLYMER PARTICLES

(75) Inventors: Rüdiger Funk, Niedernhausen (DE); Matthias Weismantel, Jossgrund-Oberndorf (DE); Sylvia Bertha, Frankenthal (DE)

(73) Assignee: BASF SE, Ludwigshafen (DE)

( * ) Notice: Subject to any disclaimer, the term of this patent is extended or adjusted under 35 U.S.C. 154(b) by 279 days.

(21) Appl. No.: 13/003,480

(22) PCT Filed: Jul. 3, 2009

(86) PCT No.: PCT/EP2009/058416
§ 371 (c)(1),
(2), (4) Date: Jan. 10, 2011

(87) PCT Pub. No.: WO2010/006937
PCT Pub. Date: Jan. 21, 2010

(65) Prior Publication Data
US 2011/0118430 A1    May 19, 2011

(30) Foreign Application Priority Data
Jul. 15, 2008   (EP) .................................. 08160430

(51) Int. Cl.
*C08F 8/00* (2006.01)
*C08F 20/06* (2006.01)

(52) U.S. Cl. ............... 525/329.7; 525/329.4; 525/330.2; 525/374; 525/375; 525/384; 526/65; 526/73; 526/88; 526/303.1; 526/317.1

(58) Field of Classification Search ............... 525/329.7, 525/329.4, 330.2, 374, 375, 384; 526/65, 526/73, 88, 303.1, 317.1
See application file for complete search history.

(56) References Cited

U.S. PATENT DOCUMENTS

| | | |
|---|---|---|
| 5,064,582 A | 11/1991 | Sutton et al. |
| 5,478,879 A | 12/1995 | Kajikawa et al. |
| 5,486,569 A | 1/1996 | Henderson et al. |
| 7,750,085 B2 | 7/2010 | Torii et al. |

FOREIGN PATENT DOCUMENTS

| | | |
|---|---|---|
| CA | 2195373 A1 | 7/1997 |
| EP | 0 463 388 A1 | 1/1992 |
| EP | 0 496 594 A2 | 7/1992 |
| EP | 0 695 763 A1 | 2/1996 |
| EP | 0 785 224 A2 | 7/1997 |
| EP | 1 878 761 A1 | 1/2008 |
| WO | WO-2004/018006 A1 | 3/2004 |
| WO | WO 2004018006 A1 * | 3/2004 |

OTHER PUBLICATIONS

Buchholz et al. (eds), Modern Superabsorbent Polymer Technology, Wiley-VCH, pp. 71-103 (1998).
International Search Report for corresponding International Application No. PCT/EP2009/058416, mailing date Oct. 2, 2009.
Ullmann's Encyclopedia of Industrial Chemistry, Wiley-VCH, 6th edition, vol. 35, pp. 73-93 (2003).

* cited by examiner

*Primary Examiner* — Michael M Bernshteyn
(74) *Attorney, Agent, or Firm* — Marshall, Gerstein & Borun LLP

(57) ABSTRACT

A process for producing water-absorbing polymer particles, comprising polymerization, drying, comminution, classification and recycling of the undersize obtained in the classification, wherein the recycled undersize is coated with a reducing agent and/or inorganic particles.

13 Claims, No Drawings

METHOD FOR PRODUCING WATER-ABSORBING POLYMER PARTICLES

CROSS-REFERENCE TO RELATED APPLICATIONS

This is the U.S. national phase of International Application No. PCT/EP2009/058416, filed Jul. 3, 2009, which claims the benefit of European patent Application No. 08160430.8, filed Jul. 15, 2008.

DESCRIPTION

The present invention relates to a process for producing water-absorbing polymer particles, comprising polymerization, drying, comminution, classification and recycling of the undersize obtained in the classification, wherein the recycled undersize is coated with a reducing agent and/or inorganic particles.

Water-absorbing polymers are used to produce diapers, tampons, sanitary napkins and other hygiene articles, but also as water-retaining agents in market gardening. The water-absorbing polymers are also referred to as superabsorbents and consist of hydrophilic polymers which are so highly crosslinked that they are no longer soluble.

The preparation of the water-absorbing polymers is described, for example, in the monograph "Modern Superabsorbent Polymer Technology", F. L. Buchholz and A. T. Graham, Wiley-VCH, 1998, pages 71 to 103, and in Ullmann's Encyclopedia of Industrial Chemistry, 6th edition, volume 35, pages 73 to 93.

The properties of the water-absorbing polymer particles can be adjusted, for example, via the amount of crosslinker used. With increasing amount of crosslinker, the centrifuge retention capacity (CRC) falls and the absorption under a pressure of 21.0 g/cm$^2$ (AUL0.3 psi) passes through a maximum.

To improve the performance properties, for example permeability of the swollen gel bed (SFC) in the diaper and absorption under a pressure of 49.2 g/cm$^2$ (AUL0.7 psi), water-absorbing polymer particles are generally surface postcrosslinked. This increases the degree of crosslinking of the particle surface, which allows the absorption under a pressure of 49.2 g/cm$^2$ (AUL0.7 psi) and the centrifuge retention capacity (CRC) to be at least partially decoupled. This surface postcrosslinking can be carried out in the aqueous gel phase. However, preference is given to surface coating dried, ground and screened-off polymer particles (base polymer) with a surface postcrosslinker and thermally surface postcrosslinking them.

The water-absorbing polymers are used as a pulverulent, particulate product, preferably in the hygiene sector. Here, for example, particle sizes between 150 and 850 μm are used, and the particulate polymer material is classified to these particle sizes as early as in the production process. This is done by using continuous screening machines with at least two screens, using screens with mesh sizes of 150 and 850 μm. Particles with a particle size of up to 150 μm fall through both screens and are collected as undersize at the bottom of the screening machine, discharged and recycled. Particles with a particle size of greater than 850 μm remain as oversize on the uppermost screen and are discharged, ground again and recycled. The product fraction with a particle size of from greater than 150 to 850 μm is removed as midsize between the two screens of the screening machine.

The undersize and oversize obtained in the classification is typically recycled into the production process. The recycling of the undersize is described, for example, in EP 0 463 388 A1, EP 0 496 594 A2, EP 0 785 224 A2, EP 1 878 761 A1 and U.S. Pat. No. 5,064,582.

EP 0 463 388 A1 states that addition of a small amount of undersize to polymer gels with a low solids content can result in pumpable polymer gels with a high solids content.

EP 0 496 594 A2 teaches the recycling of the undersize into the polymerization reactor.

EP 0 785 224 A2 describes the recycling of the undersize into the polymer gel formed in the polymerization, with addition of surfactants.

EP 1 878 761 A1 discloses a process for recycling undersize coated with water-soluble polyvalent metal salts. The undersize can be mixed into the polymer gel, for example by means of a kneader.

U.S. Pat. No. 5,064,582 discloses a process for recycling undersize, wherein the undersize is mixed with water before the recycling.

It was an object of the present invention to provide an improved process for recycling the undersize obtained in the production of water-absorbing polymer particles.

The object was achieved by a process for producing water-absorbing polymer particles by polymerizing a monomer solution or suspension comprising a) at least one ethylenically unsaturated monomer bearing acid groups,
b) at least one crosslinker,
c) at least one initiator,
d) optionally one or more ethylenically unsaturated monomers copolymerizable with the monomers specified under a) and
e) optionally one or more water-soluble polymers, comprising the steps of i) polymerizing the monomer solution or suspension to give a polymer gel,
ii) drying the polymer gel,
iii) comminuting the dried polymer gel and
iv) classifying to remove undersize, the removed undersize being recycled at least partially before step ii), wherein at least a portion of the recycled undersize is coated with at least one reducing agent and/or inorganic particles.

The water-absorbing polymer particles are preferably surface postcrosslinked before the classification iv), and more preferably additionally classified before the surface postcrosslinking, which likewise removes undersize.

The undersize removed before the surface postcrosslinking and the undersize removed after the surface postcrosslinking are preferably recycled into the process, more preferably as a mixture. The mixing ratio is not subject to any restriction, but the aim should be a maximum proportion of surface nonpostcrosslinked undersize.

The undersize for recycling is preferably coated with the reducing agent and/or the inorganic particles before the classification iv), more preferably after the surface postcrosslinking. In this case, the undersize is coated together with the product fraction. This leads to a further improvement in the product properties.

It is particularly advantageous to recycle the undersize after the polymerization i), i.e. into a separate apparatus between polymerization reactor and drier. Suitable apparatus for this purpose is, for example, kneaders and extruders.

The amount of undersize coated with the reducing agent and/or inorganic particles which is recycled is preferably from 1 to 20% by weight, more preferably from 2 to 15% by weight, most preferably from 5 to 10% by weight, based in each case on the solids content of the monomer solution. The solids content is the sum of all constituents which are nonvolatile after the polymerization. These are the monomer a), the crosslinker b), the initiator c), the monomer d) and the polymer e).

The amount of reducing agent is preferably from 0.01 to 5% by weight, more preferably from 0.05 to 2% by weight, most preferably from 0.1 to 1% by weight, based in each case on the coated undersize.

The reducing agents are not subject to any restriction. Suitable reducing agents are, for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to salts of hypophosphorous acid, for example sodium hypophosphite, and salts of sulfinic acids, for example the disodium salt of 2-hydroxy-2-sulfinatoacetic acid.

The reducing agents are typically used in the form of a solution in a suitable solvent, preferably water.

The amount of inorganic particles is preferably from 0.05 to 5% by weight, more preferably from 0.1 to 2% by weight, most preferably from 0.2 to 1% by weight, based in each case on the coated undersize.

Suitable inorganic particles are, for example, aluminum sulfate, magnesium sulfate, clay minerals, calcium sulfate, magnesium carbonate, potassium aluminum sulfate (potassium alum), aluminum nitrate, aluminum chloride, sodium aluminum sulfate (sodium alum), magnesium oxide, aluminum oxide, diatomaceous earth, titanium dioxide, sand and zeolites. However, preference is given to using water-insoluble inorganic particles, for example fumed silica and water-insoluble metal phosphates such as calcium phosphate. "Water-insoluble" here means a solubility in water at 23° C. of less than 1 g/100 g of water, preferably of less than 0.5 g/100 g of water, more preferably of less than 0.1 g/100 g of water, most preferably of less than 0.05 g/100 g of water.

The inorganic particles have a mean particle size of preferably less than 400 µm, more preferably less than 100 µm, most preferably less than 50 µm. Water-insoluble inorganic particles can also be used in the form of an aqueous dispersion.

Crystalline inorganic solids preferably have a particle size of greater than 10 µm. The apparatus usable for coating the undersize is not subject to any restriction. Suitable mixers with moving mixing tools are, for example, screw mixers, disk mixers and paddle mixers. Mixers with rotating mixing tools are subdivided into vertical mixers and horizontal mixers according to the position of the axis of rotation relative to the product flow direction. Advantageously, horizontal mixers are used. Particular preference is given to using continuous horizontal mixers (flow mixers).

The residence time in the horizontal mixer is preferably from 1 to 180 minutes, more preferably from 2 to 60 minutes, most preferably from 5 to 20 minutes.

The peripheral speed of the mixing tools in the horizontal mixer is preferably from 0.1 to 10 m/s, more preferably from 0.5 to 5 m/s, most preferably from 0.75 to 2.5 m/s.

The water-absorbing polymer particles are moved within the horizontal mixer at a velocity which corresponds to a Froude number of preferably from 0.01 to 6, more preferably from 0.05 to 3, most preferably from 0.1 to 0.7.

For the coating, preference is given to using a thermally insulated and/or trace-heated two-substance nozzle, which advantageously ends below the product bed surface.

The preparation of the usually water-insoluble water-absorbing polymer particles will be illustrated in detail hereinafter.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1 WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mmol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylatecl glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). With rising crosslinker content, the centrifuge retention capacity (CRC) falls and the absorption under a pressure of 21.0 g/cm$^2$ (AUL0.3 psi) passes through a maximum.

The initiators c) may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors for the polymerization i) are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 95 mol %, more preferably from 30 to 80 mol %, most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The drying ii) of the polymer gel is then preferably carried out with a belt drier until the residual moisture content is preferably from 0.5 to 15% by weight, more preferably from 1 to 10% by weight, most preferably from 2 to 8% by weight, the residual moisture content being determined by the EDANA (European Disposables and Nonwovens Association) recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is comminuted and classified. For the comminution iii), typically single- or multistage roll mills, preferably two- or three-stage roll mills, pin mills, hammer mills or vibratory mills, are used. For the classification iv), typically tumbling screening machines are used.

The mean particle size of the polymer particles removed as the product fraction is preferably at least 200 µm, more preferably from 250 to 600 µm, very particularly from 300 to 500 µm. The mean particle size of the product fraction may be determined by means of the EDANA (European Disposables and Nonwovens Association) recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 µm is preferably at least 90% by weight, more preferably at least 95% by weight, most preferably at least 98% by weight.

Polymer particles with too small a particle size lower the permeability (SFC). The proportion of excessively small polymer particles ("fines") should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

The proportion of particles having a particle size of at most 850 µm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the comminution iii) of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or p-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably from 0.001 to 2% by weight, more preferably from 0.02 to 1% by weight, most preferably from 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations.

The amount of polyvalent cation used is, for example, from 0.001 to 1.5% by weight, preferably from 0.005 to 1% by weight, more preferably from 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting behavior and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The thermal drying is preferably carried out in contact driers, more preferably paddle driers, most preferably disk driers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany) and Nara paddle driers (NARA Machinery Europe; Frechen; Germany). Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range from 100 to 250° C., preferably from 120 to 220° C., more preferably from 130 to 210° C., most preferably from 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or subsequently moistened. Suitable coatings for improving the swell rate and the permeability (SFC) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

When such a coating or subsequent moistening is carried out, the surface postcrosslinked polymer particles are advantageously not classified again until after the coating or subsequent moistening.

The water-absorbing polymer particles produced by the process according to the invention have a moisture content of preferably from 0 to 15% by weight, more preferably from 0.2 to 10% by weight, most preferably from 0.5 to 8% by weight, the water content being determined by the EDANA (European Disposables and Nonwovens Association) recommended test method No. WSP 230.2-05 "Moisture Content".

The water-absorbing polymer particles produced by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by the EDANA (European Disposables and Nonwovens Association) recommended test method No. WSP 241.2-05 "Centrifuge Retention Capacity".

The water-absorbing polymer particles produced by the process according to the invention have an absorption under a pressure of 49.2 $g/cm^2$ (AUL0.7 psi) of typically at least 15 g/g, preferably at least 20 g/g, preferentially at least 22 g/g, more preferably at least 24 g/g, most preferably at least 26 g/g. The absorption under a pressure of 49.2 $g/cm^2$ (AUL0.7 psi) of the water-absorbing polymer particles is typically less than 35 µg. The absorption under a pressure of 49.2 $g/cm^2$ (AUL0.7 psi) is determined analogously to the EDANA (European Disposables and Nonwovens Association) recommended test method No. WSP 242.2-05 "Absorption under Pressure", except that a pressure of 49.2 $g/cm^2$ (AUL0.7 psi) is established instead of a pressure of 21.0 $g/cm^2$ (AUL0.3 psi).

Methods:

The analyses should, unless stated otherwise, be performed at an ambient temperature of 23±2° C. and a relative air humidity of 50±10%. The water-absorbing polymer particles are mixed thoroughly before the analysis.

Residual Monomers

The residual monomers (Remos) are determined by the EDANA (European Disposables and Nonwovens Association) recommended test method No. WSP 210.2-05 "Residual Monomers".

Particle Size Distribution

The particle size distribution (PSD) is determined by the EDANA (European Disposables and Nonwovens Association) recommended test method No. WSP 220.2-05 "Particle Size Distribution".

Centrifuge Retention Capacity

The centrifuge retention capacity (CRC) is determined by the EDANA (European Disposables and Nonwovens Association) recommended test method No. WSP 241.2-05 "Centrifuge Retention Capacity".

Absorption Under a Pressure of 21.0 $g/cm^2$

The absorption under a pressure of 21.0 $g/cm^2$ (AUL0.3 psi) is determined by the EDANA (European Disposables and Nonwovens Association) recommended test method No. WSP 242.2-05 "Absorption under Pressure".

Absorption Under a Pressure of 49.2 $g/cm^2$

The absorption under a pressure of 49.2 $g/cm^2$ (AUL0.7 psi) is determined analogously to the EDANA (European Disposables and Nonwovens Association) recommended test method No. WSP 242.2-05 "Absorption under Pressure", except that a pressure of 49.2 $g/cm^2$ (AUL0.7 psi) is established instead of a pressure of 21.0 $g/cm^2$ (AUL0.3 psi).

Free Swell Rate

To determine the free swell rate (FSR), 1.00 g ($=W_1$) of the dry water-absorbing polymer particles is weighed into a 25 ml beaker and distributed evenly over its base. Then 20 ml of a 0.9% by weight sodium chloride solution are metered into a second beaker. The contents of this beaker are added rapidly to the first and a stopwatch is started. As soon as the last drop of salt solution has been absorbed, which is recognized by the disappearance of the reflection on the liquid surface, the stopwatch is stopped. The exact amount of liquid which has been poured out of the second beaker and absorbed by the polymer in the first beaker is determined accurately by reweighing the second beaker (=$W_2$). The period required for the absorption, which has been measured with the stopwatch, is referred to as t.

From this, the free swell rate (FSR) is calculated as follows:

$$FSR[g/gs]=W_2/(W_1 \times t)$$

CIE Color Number (L* a* b*)

The color analysis was carried out according to the CIELAB method (Hunterlab, volume 8, 1996, issue 7, pages 1 to 4). This method describes the colors via the coordinates L*, a* and b* of a three-dimensional system. L* indicates the brightness, where L*=0 means black and L*=100 white. The values of a* and b* indicate the position of the color on the red/green and yellow/blue color axes respectively, where +a* means red, −a* means green, +b* means yellow and −b* means blue. A "LabScan XE S/N LX17309" colorimeter was used (HunterLab, Reston, US).

The following instrument settings were used: light source C; observer 2°; geometry 45/0.

The color analysis corresponds to the three-area method to DIN 5033-6.

The Hunter 60 value (H60) is a measure of the whiteness of surfaces and is defined as L*-3b*, i.e. the darker and the more yellowish a color is, the lower the value.

The EDANA test methods are obtainable, for example, from the European Disposables and Nonwovens Association, Avenue Eugene Plasky 157, B-1030 Brussels, Belgium.

EXAMPLES

Example 1

Preparation of the Base Polymer 1028 g of a 37.3% by weight aqueous sodium acrylate solution, 98 g of acrylic acid, 254 g of water and 0.59 g of 3-tuply ethoxylated glyceryl triacrylate were weighed into a 2000 ml metal cup. The degree of neutralization was 75 mol %. The metal cup was sealed with Parafilm® and inertized with 150 l/h of nitrogen. During the inertization, the monomer solution was cooled to −0.5° C. Subsequently, 6.47 g of a 10% by weight aqueous solution of sodium persulfate and 5.88 g of a 1% by weight aqueous solution of hydrogen peroxide were added successively.

The monomer solution was transferred by means of a funnel into a glass dish with a diameter of 190 mm. The glass dish was covered with a polymer film and likewise inertized with 150 l/h of nitrogen. In addition, the monomer solution was stirred in the glass dish by means of a magnetic stirrer bar. Subsequently, by means of a disposable syringe, 5.88 g of a 1% by weight aqueous solution of Brüggolite® FF6 (disodium salt of 2-hydroxy-2-sulfinatoacetic acid) were metered into the monomer solution. After the start of the reaction, the magnetic stirrer was switched off.

After a reaction time of 30 minutes, the polymer gel was removed and comminuted with an extruder with a perforated plate (hole diameter 6 mm), sprayed with 17.6 g of a 1% by weight aqueous solution of sodium bisulfite and extruded twice.

The gel was dried at 160° C. in a forced-air drying cabinet for one hour. The loading of the metal sheets with polymer gel was 0.59 g/cm². This was followed by comminuting with a four-stage roll mill with a gap width of 5 mm, 1000 μm, 600 μm and 400 μm, and screening off to from 150 to 850 μm (base polymer).

The resulting water-absorbing polymer particles were analyzed. The results are compiled in Table 1.

A portion of the base polymer was comminuted by means of a rotor mill (Retsch® ZM200) to a particle size of less than 150 μm (undersize).

Example 2

Comparative Example 1028 g of a 37.3% by weight aqueous sodium acrylate solution, 98 g of acrylic acid, 254 g of water and 0.59 g of 3-tuply ethoxylated glyceryl triacrylate were weighed into a 2000 ml metal cup. The degree of neutralization was 75 mol %. The metal cup was sealed with Parafilm® and inertized with 150 l/h of nitrogen. During the inertization, the monomer solution was cooled to −0.5° C. Subsequently, 6.47 g of a 10% by weight aqueous solution of sodium persulfate and 5.88 g of a 1% by weight aqueous solution of hydrogen peroxide were added successively.

The monomer solution was transferred by means of a funnel into a glass dish with a diameter of 190 mm. The glass dish was covered with a polymer film and likewise inertized with 150 l/h of nitrogen. In addition, the monomer solution was stirred in the glass dish by means of a magnetic stirrer bar. Subsequently, by means of a disposable syringe, 5.88 g of a 1% by weight aqueous solution of Brüggolite®FF6 (disodium salt of 2-hydroxy-2-sulfinatoacetic acid) were metered into the monomer solution. After the start of the reaction, the magnetic stirrer was switched off.

After a reaction time of 30 minutes, the polymer gel was removed and comminuted with an extruder with a perforated plate (hole diameter 6 mm), sprayed with 17.6 g of a 1% by weight aqueous solution of sodium bisulfite and extruded again. Subsequently, a total of 84 g of undersize from Example 1 in two portions was powdered by means of a 180 μm screen and a spoon, and extruded for a third time.

The gel was dried at 160° C. in a forced-air drying cabinet for one hour. The loading of the metal sheets with polymer gel was 0.59 g/cm². This was followed by comminuting with a four-stage roll mill with a gap width of 5 mm, 1000 μm, 600 μm and 400 μm, and screening off to from 150 to 850 μm (base polymer).

The resulting water-absorbing polymer particles were analyzed. The results are compiled in Table 1.

Example 3

The procedure was as in Example 2. The undersize incorporated into the polymer gel obtained after the polymerization was coated with sodium hypophosphite before the recycling.

The resulting water-absorbing polymer particles were analyzed. The results are compiled in Table 1.

Preparation of the Undersize Coated with Sodium Hypophosphite:

For this purpose, 84 g of undersize from Example 1 were introduced into a food processor and stirred. By means of a two-substance nozzle, 16.8 g of a 3% by weight aqueous sodium hypophosphite solution were sprayed onto the stirred undersize and the mixture was stirred for a further 5 minutes. The coated undersize was distributed onto four Petri dishes (diameter 13.5 cm; height 2.5 cm) and dried at 150° C. in a forced-air drying cabinet for 30 minutes. This was followed by deagglomeration in a coffee grinder and screening-off to less than 150 μm.

Example 4

The procedure was as in Example 2. The undersize incorporated into the polymer gel obtained after the polymerization was coated with Brüggolite® FF7 (Brüggemann Chemicals; Heilbronn; Germany) before the recycling. Brüggolit® FF7 is a mixture of the disodium salt of 2-hydroxy-2-sulfinatoacetic acid, the disodium salt of 2-hydroxy-2-sulfonatoacetic acid and sodium bisulfite.

The resulting water-absorbing polymer particles were analyzed. The results are compiled in Table 1.

Preparation of the undersize coated with Brüggolite® FF7:

For this purpose, 84 g of undersize from Example 1 were introduced into a food processor and stirred. By means of a two-substance nozzle, 8.4 g of a 1% by weight aqueous solution of Brüggolite® FF7 were sprayed onto the stirred undersize and the mixture was stirred for a further 5 minutes. The coated undersize was distributed onto four Petri dishes (diameter 13.5 cm; height 2.5 cm) and dried in a forced-air drying cabinet at 150° C. for 30 minutes. This was followed by deagglomeration in a coffee grinder and screening-off to less than 150 μm.

Example 5

The procedure was as in Example 2. The undersize incorporated into the polymer gel obtained after the polymerization was coated with Sipernat® D17 (Evonik Industries AG; Essen; Germany) before the recycling. Sipernat® D17 is fumed silica.

The resulting water-absorbing polymer particles were analyzed. The results are compiled in Table 1.

Preparation of the Undersize Coated with Sipernat® D17:

For this purpose, 84 g of undersize and 0.25 g of Sipernat® 017 were introduced into a 250 ml glass bottle and homogenized with a rolling mixer for 30 minutes.

Example 6

The procedure was as in Example 2. The undersize incorporated into the polymer gel obtained after the polymerization was coated with C 13-09 tricalcium phosphate (Chemische Fabrik Budenheim KG; Budenheim; Germany) before the recycling.

The resulting water-absorbing polymer particles were analyzed. The results are compiled in Table 1.

Preparation of the undersize coated with C 13-09 tricalcium phosphate:

For this purpose, 84 g of undersize and 0.42 g of C 13-09 calcium phosphate were introduced into a 250 ml glass bottle and homogenized with a rolling mixer for 30 minutes.

Example 7

Surface Postcrosslinking

The base polymer prepared in Example 1 was surface postcrosslinked. For this purpose, 100 g of base polymer were introduced into a food processor and stirred. By means of a two-substance nozzle, 3.15 g of an aqueous solution (0.15 g of 2-hydroxyethyl-2-oxazolidinone, 0.9 g of isopropanol and 2.1 g of water) were sprayed onto the stirred base polymer within one minute and the mixture was stirred for a further 5 minutes. The coated base polymer was distributed homogenously onto two Petri dishes (diameter 20 cm; height 2.5 cm) and surface postcrosslinked in a forced-air drying cabinet at 170° C. for 60 minutes.

After the thermal surface postcrosslinking, a screen with mesh size 850 μm was used to remove oversize, and the oversize was determined quantitatively and discarded. The surface postcrosslinked water-absorbing polymer particles with a particle size of 850 μm and less which were obtained in this way were analyzed. The results are compiled in Table 2.

Example 8

Comparative Example

The procedure was as in Example 7. The base polymer prepared in Example 2 was used.

The resulting surface postcrosslinked water-absorbing polymer particles were analyzed. The results are compiled in Table 2.

Examples 9 to 12

The procedure was as in Example 7. The base polymers prepared in Examples 3 to 6 were used.

The resulting surface postcrosslinked water-absorbing polymer particles were analyzed. The results are compiled in Table 2.

TABLE 1

| | | Base polymers | | | | | | |
|---|---|---|---|---|---|---|---|---|
| | | CRC | AUL0.3 psi | FSR | Remos | CIE color number | | |
| Ex. | Recycling | [g/g] | [g/g] | [g/gs] | [ppm] | L* | b* | H60 |
| 1 | none | 42.1 | 7.1 | 0.27 | 340 | 90.7 | 7.4 | 68.4 |
| 2*) | uncoated undersize | 39.8 | 7.3 | 0.31 | 509 | 91.1 | 7.9 | 67.5 |
| 3 | undersize coated with sodium hypophosphite | 40.6 | 6.9 | 0.30 | 821 | 91.1 | 6.5 | 71.7 |
| 4 | undersize coated with Brüggolite ® FF7 | 39.9 | 7.4 | 0.30 | 617 | 91.3 | 7.2 | 69.7 |
| 5 | undersize coated with Sipernat ® D17 | 40.2 | 7.2 | 0.28 | 313 | 91.7 | 7.8 | 68.4 |
| 6 | undersize coated with C 13-09 tricalcium phosphate | 39.4 | 7.5 | 0.29 | 642 | 91.3 | 7.2 | 69.8 |

*)comparative example

TABLE 2

| | | Surface postcrosslinking | | | | | | | |
|---|---|---|---|---|---|---|---|---|---|
| | | CRC | AUL0.7 psi | FSR | Remos | Particles >850 μm | CIE color number | | |
| Ex. | Recycling | [g/g] | [g/g] | [g/gs] | [ppm] | [% by wt.] | L | b | H60 |
| 7 | none | 38.5 | 8.0 | 0.31 | 918 | 3.5 | 88.6 | 7.9 | 64.8 |
| 8*) | uncoated undersize | 35.3 | 8.5 | 0.30 | 1131 | 4.5 | 89.7 | 8.2 | 65.0 |
| 9 | undersize coated with sodium hypophosphite | 35.4 | 7.8 | 0.33 | 871 | 1.4 | 90.1 | 6.8 | 69.6 |
| 10 | undersize coated with Brüggolite ® FF7 | 36.5 | 7.7 | 0.35 | 638 | 0.5 | 90.0 | 7.6 | 67.1 |
| 11 | undersize coated with Sipernat ® D17 | 35.0 | 8.8 | 0.32 | 697 | 1.8 | 90.4 | 8.1 | 66.1 |
| 12 | undersize coated with C 13-09 tricalcium phosphate | 35.4 | 8.5 | 0.32 | 776 | 2.1 | 90.5 | 7.7 | 67.3 |

*)comparative example

The results demonstrate that the surface postcrosslinked polymer particles produced by the process according to the invention have a higher free swell rate, lower residual monomers, lower agglomerates (particles >850 μm) and a whiter color with low yellowness (H60).

The invention claimed is:

1. A process for producing water-absorbing polymer particles by polymerizing a monomer solution or suspension comprising
    a) at least one ethylenically unsaturated monomer bearing an acid group,
    b) at least one crosslinker,
    c) at least one initiator,
    d) optionally one or more ethylenically unsaturated monomer copolymerizable with the monomer specified under a), and
    e) optionally one or more water-soluble polymer,
    comprising the steps of
    i) polymerizing the monomer solution or suspension to give a polymer gel,
    ii) drying the polymer gel,
    iii) comminuting the dried polymer gel, and
    iv) classifying to remove undersize particles,
    the removed undersize particles being recycled at least partially before step ii), wherein at least a portion of the recycled undersize particles is coated with at least one of a reducing agent and inorganic particles, wherein the inorganic particles comprise fumed silica or insoluble salts of phosphoric acid.

2. The process according to claim 1, wherein the water-absorbing polymer particles are surface postcrosslinked before step iv).

3. The process according to claim 2, wherein step iii) is followed and the surface postcrosslinking is preceded by additional classification and undersize particle removal.

4. The process according to claim 3, wherein the undersize particles removed before the surface postcrosslinking are recycled together with the undersize particles removed in step iv).

5. The process according to claim 1, wherein the portion of the recycled undersize particles coated with a reducing agent and/or inorganic particles is coated before step iv).

6. The process according to claim 2, wherein the portion of the recycled undersize particles coated with a reducing agent and/or inorganic particles is coated after the surface postcrosslinking.

7. The process according to claim 1, wherein the undersize particles removed are recycled after step i).

8. The process according to claim 1, wherein the portion of the recycled undersize particles coated with the reducing agent and/or inorganic particles is from 1 to 20% by weight, based on a solids content of the monomer solution or suspension.

9. The process according to claim 1, wherein the undersize particles coated with a reducing agent are coated with from 0.01 to 5% by weight of the reducing agent, based on the undersize particles.

10. The process according to claim 1, wherein the reducing agent comprises a salt of hypophosphorous acid or a salt of a sulfinic acid.

11. The process according to claim 1, wherein the undersize particles coated with inorganic particles are coated with from 0.05 to 2% by weight of inorganic particles, based on the undersize particles.

12. The process according to claim 1, wherein the monomer a) comprises partially neutralized acrylic acid.

13. The process according to claim 1, wherein the water-absorbing polymer particles have a centrifuge retention capacity of at least 15 g/g.

* * * * *